(12) United States Patent
Park et al.

(10) Patent No.: US 9,069,082 B2
(45) Date of Patent: Jun. 30, 2015

(54) METHOD FOR DETECTION OF RADIATION-INDUCED DAMAGE TO BIOMATERIAL USING MAGNETIC SENSOR AND MAGNETIC SENSOR BIOCHIP FOR BIODOSIMETRY USING THE SAME

(71) Applicant: Korea Atomic Energy Research Institute, Daejeon (KR)

(72) Inventors: Deuk-Gun Park, Daejeon (KR); Hoon Song, Daejeon (KR); Deok-Hyun Lee, Daejeon (KR); Yong-Hwan Jeong, Daejeon (KR)

(73) Assignee: Korea Atomic Energy Research Institute, Daejeon (KR)

( * ) Notice: Subject to any disclaimer, the term of this patent is extended or adjusted under 35 U.S.C. 154(b) by 261 days.

(21) Appl. No.: 13/907,775

(22) Filed: May 31, 2013

(65) Prior Publication Data
US 2013/0323844 A1 Dec. 5, 2013

(30) Foreign Application Priority Data
May 31, 2012 (KR) .................. 10-2012-0058872

(51) Int. Cl.
G01N 23/00 (2006.01)
G01T 1/04 (2006.01)
G01N 33/543 (2006.01)

(52) U.S. Cl.
CPC ............ *G01T 1/04* (2013.01); *G01N 33/54306* (2013.01); *G01N 33/54333* (2013.01)

(58) Field of Classification Search
None
See application file for complete search history.

(56) References Cited

U.S. PATENT DOCUMENTS

2004/0253744 A1   12/2004   Rife et al.
2008/0138823 A1   6/2008    Staab

FOREIGN PATENT DOCUMENTS

JP     2007-522435 A      8/2007
KR   10-2007-0107347 A   11/2007

OTHER PUBLICATIONS

Notice of Allowance dated Nov. 29, 2013 of corresponding Korean Patent Application No. 10-2012-0058872—5 pages.

*Primary Examiner* — Robert Xu
(74) *Attorney, Agent, or Firm* — Knobbe Martens Olson & Bear, LLP

(57) ABSTRACT

Disclosed is a method for the detection of radiation-induced damage on a biomaterial using a magnetic sensor, and a magnetic sensor biochip for biodosimetry. Designed to utilize a magnetic sensor in detecting damage to biomaterials in vitro, the method and magnetic sensor biochip can accurately determine the degree of damage irrespective of the self-recovery of the organism. Thanks to their high sensitivity, the method and biochip can detect the biomaterial damage by exposure to even a low dose of radiation.

7 Claims, 5 Drawing Sheets

METHOD FOR DETECTION OF RADIATION-INDUCED DAMAGE TO BIOMATERIAL USING MAGNETIC SENSOR AND MAGNETIC SENSOR BIOCHIP FOR BIODOSIMETRY USING THE SAME

BACKGROUND OF THE INVENTION

1. Field of the Invention

The present invention relates to a method for detecting radiation-induced damage to a biomaterial using a magnetic sensor, and a magnetic sensor biochip for biodosimetry using the same.

2. Description of the Related Art

A biochip is a dense, two-dimensional grid of biosensors including DNAs, antibodies, ligands, and the like which are typically deposited on a flat passive or active substrate, such as glass, plastic, etc. Biochips are largely divided into genotyping chips for detecting specific genes; gene expression chips for examining an expression pattern of genes associated with specific diseases; and microfluidic chips for detecting the presence and/or reaction of biologically active substances in fluid biosamples such as blood, urine, etc. Given an active substrate that consists of, for example, integrated electronics, the microchip can also automatically analyze various information including gene and protein information detected by the deposited biosensors on a large scale, and rapidly and readily detect the presence and/or function of biologically active substances such as DNA, antibodies, ligands, etc. In recent years, biochips have actively found applications in various fields including gene and protein research, medicines, agriculture, foods, environments, and chemical industries.

Dosimeters, particularly, radiation dosimeters measure cumulative exposure to radiation over a period of time. Representative among the radiation dosimeters are physical and biological dosimeters. A physical dosimeter utilizes the ionizing effect of radiation, while a biodosimeter measures the influence of radiation on organisms by analyzing, for example, blood taken from an organism exposed to radiation.

A physical dosimeter, which is a device designed to utilize electronic equipment to determine the amount of radiation emitted from a source of ionizing radiation, can accurately measure an absorbed dose, that is, an amount of energy imparted to matter by ionizing radiation, in real time. There are various commercially available products of physical dosimeters including film badges, glass dosimeters, thermolumenescence dosimeters, and pocket dosimeters. Because a physical dosimeter is directly irrelevant to an organism exposed to radiation, it cannot inform the effect of radiation on the organism. In contrast, a biodosimeter, a device designed to analyze blood or cells of a radiation-exposed organism, can explain the effect of radiation on the organism, but suffers from the disadvantage of requiring a lot of time for analysis, with the following consequent problems. Self recovery may take place during the analysis, making it difficult to accurately determine the degree of radiation exposure. In addition, because the biological effect of radiation is measured a certain time after radiation exposure, there is a controversy with regard to whether the biological change analyzed is attributed to radiation or other factors. Accordingly, active research has recently been directed towards the development of various biodosimeters as solutions to the abovementioned problems. For example, U.S. Patent Publication No. 2010-0144558 discloses a biodosimeter for measuring expression levels of genes depending on radiation dose. This biodosimeter targets changes in gene expression of blood, but cannot measure radiation-induced changes of biomaterials themselves, that is, DNA damage, white cell counts, etc.

As such, few biodosimeters capable of accurately measuring the change of biomaterials by radiation exposure have been developed thus far, and there is therefore pressing need for such a biodosimeter.

SUMMARY OF THE INVENTION

Accordingly, the present invention has been made keeping in mind the above problems encountered in the prior art, and it is an object of the present invention is to provide a method for detecting radiation-induced damage of a biomaterial using a magnetic sensor, and a magnetic sensor biochip using the same, which both reveal an approach to the development of a biodosimeter capable of accurately measuring a biomaterial change by radiation exposure with high sensitivity.

However, the objects to be achieved by the present invention are not limited to the foregoing, and objects and advantages other than those set forth above will be clearly understood to those skilled in the art from the following description.

In accordance with an aspect thereof, the present invention provides a method for detecting radiation-induced damage of a biomaterial, comprising: a) coupling a linker conjugated to a surface of a magnetic sensor with a magnetic nanoparticle-conjugated target biomaterial to form a complex; b) exposing the coupled complex to radiation; and c) measuring radiation-induced damage to the coupling between the linker and the biomaterial in an electrical signature of the magnetic sensor.

In accordance with another aspect thereof, the present invention provides a method for detecting radiation-induced damage of a biomaterial, comprising: a) obtaining a biosample exposed to radiation; b) conjugating a magnetic nanoparticle with a target biomaterial contained in the biosample; c) coupling the magnetic nanoparticle-conjugated target biomaterial with a linker conjugated to a surface of a magnetic sensor; d) measuring the coupling between the linker and the target biomaterial in an electric signature of the magnetic sensor; and e) comparing the measurement with an electric signal of the magnetic sensor detected in a reference sample unexposed to the radiation.

In accordance with a further aspect thereof, the present invention provides a magnetic sensor biochip for biodosimetry, comprising: a magnetic sensor; a linker conjugated to a surface of the magnetic sensor; a magnetic nanoparticle; and a target biomaterial conjugated with the magnetic nanoparticle, said linker being able to couple with said target biomaterial to form a linker-target biomaterial complex, wherein when the linker-target biomaterial complex is dissociated by radiation exposure, the magnetic sensor detects a degree of the dissociation, thereby measuring radiation-induced damage.

In one embodiment of the present invention, the linker is bound to the target biomaterial.

In another embodiment of the present invention, the linker is selected from the group consisting of DNA (deoxyribonucleic acid), RNA (ribonucleic acid), a ligand, an antibody, a protein, an enzyme, and a polypeptide.

According to a further embodiment of the present invention, the target biomaterial is selected from the group consisting of DNA (deoxyribonucleic acid), RNA (ribonucleic acid), a ligand, an antibody, an antigen, a protein, an enzyme, and a polypeptide.

According to a still further embodiment of the present invention, the linker is conjugated to the magnetic sensor via an amphipathic molecule that is highly resistant to radiation.

In still another embodiment of the present invention, the radiation is selected from the group consisting of a gamma ray, a neutron ray, an X-ray, an electron ray, and an electromagnetic ray with an energy of 1 GHz or higher.

In a yet further embodiment of the present invention, the electric signature of the magnetic sensor is indicative of an absorbed dose of the radiation, based on the intensity of a stray field generated when the radiation causes the magnetic nanoparticle to secede from the magnetic sensor.

BRIEF DESCRIPTION OF THE DRAWINGS

The above and other objects, features and advantages of the present invention will be more clearly understood from the following detailed description taken in conjunction with the accompanying drawings, in which.

Objects and advantages other than those set forth above will be apparent from the following description, when read in connection with the accompanying drawings, in which.

DESCRIPTION OF EMBODIMENTS

Figure 1:
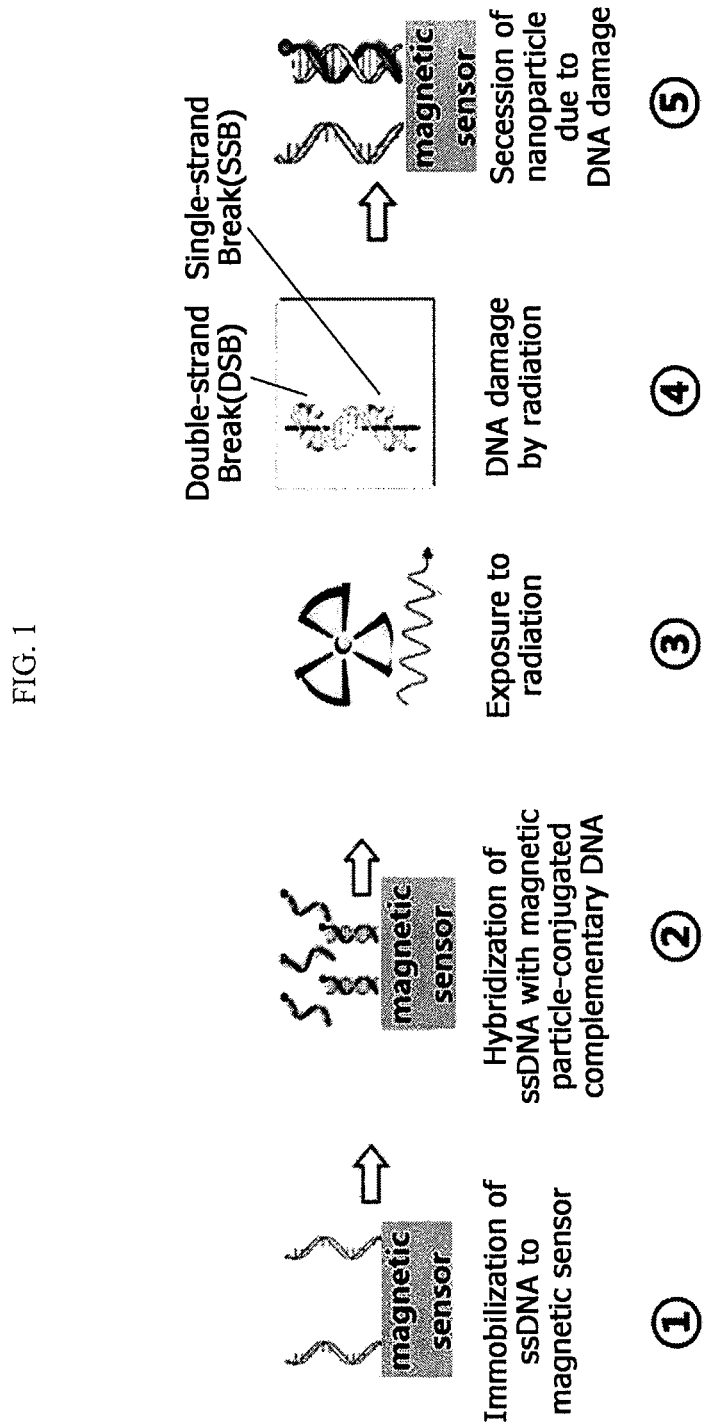
FIG. 1 is a schematic view illustrating the method for measuring radiation-induced damages on a biomaterial using a magnetic sensor.

Leading to the present invention, intensive and thorough research into a biodosimeter for measuring radiation-induced damage to biomaterials, conducted by the present inventors, resulted in the finding that a magnetic sensor in conjunction with a magnetic nanoparticle can be used in monitoring a change in the level of a material when damage is imparted thereto.

The present invention addresses a method for detecting radiation-induced damage on a biomaterial, comprising: a) coupling a linker conjugated to a surface of a magnetic sensor with a magnetic nanoparticle-conjugated target biomaterial to form a complex; b) exposing the coupled complex to radiation; and c) measuring radiation-induced damage to the coupling between the linker and the biomaterial in an electrical signature of the magnetic sensor.

In one embodiment of the present invention, single-stranded DNA was conjugated to the surface of a magnetic sensor while a complementary single-stranded DNA was conjugated with a magnetic nanoparticle through biotin-streptavidin or avidin-biotin interaction, followed by hybridizing the two DNA strands to form a DNA duplex. After exposure of the DNA duplex to radiation, signal properties of the magnetic sensor were monitored during a change in magnetic field with time. As a result, bonds between or within DNA strands are broken by radiation, so that the magnetic particle was removed from the biochip (Example 2). This data indicates that radiation exposure causes the interruption of inter- or intramolecular bonding, leading to a structural change in the biomaterial. Based on this principle, the absorbed dose of the radiation can be measured using the intensity of the stray field attributed to the radiation-induced secession of the magnetic nanoparticle from the magnetic sensor, which is applied to the development of a biodosimeter capable of measuring radiation-induced changes in biomaterials. So long as it causes a structural change in biomaterials, any radiation may be employed in the present invention. Preferred are those selected from among a gamma ray, a neutron ray, an X-ray, an electron ray, and a high-energy electromagnetic wave with a frequency of 1 GHz or higher.

Contemplated in accordance with another aspect of the present invention is a method for detecting radiation-induced damage to a biomaterial, comprising: a) obtaining a biosample exposed to radiation; b) conjugating a magnetic nanoparticle with a target biomaterial contained in the biosample; c) coupling the magnetic nanoparticle-conjugated target biomaterial with a linker conjugated to a surface of a magnetic sensor; d) measuring the coupling between the linker and the target biomaterial in an electric signature of the magnetic sensor; and e) comparing the measurement with an electric signal of the magnetic sensor detected in a reference sample unexposed to the radiation.

Also, the present invention envisages a magnetic sensor biochip for biodosimetry using the method.

The target biomaterial and the linker are coupled with each other, and may be selected from the group consisting of DNA (deoxyribonucleic acid), RNA (ribonucleic acid), ligands, antibodies, antigens, proteins, enzymes, and polypeptides.

In another embodiment of the present invention, the amphipathic molecules Sys Protein-G and ProLink were observed to bind to the surface of a gold-coated magnetic sensor and exhibit strong resistance to radiation (Example 3). Also, the amphipathic molecules can introduce various biomaterials into the magnetic sensor therethrough. No limitations are imparted to the amphipathic molecules if they are highly resistant to radiation. Preferred are Sys Protein-G and Pro-Link as the linker.

A better understanding of the present invention may be obtained through the following examples which are set forth to illustrate, but are not to be construed as limiting, the present invention.

EXAMPLES

Example 1

Fabrication of Magnetic Sensor Biochip for Biodosimeter

Figure 2:
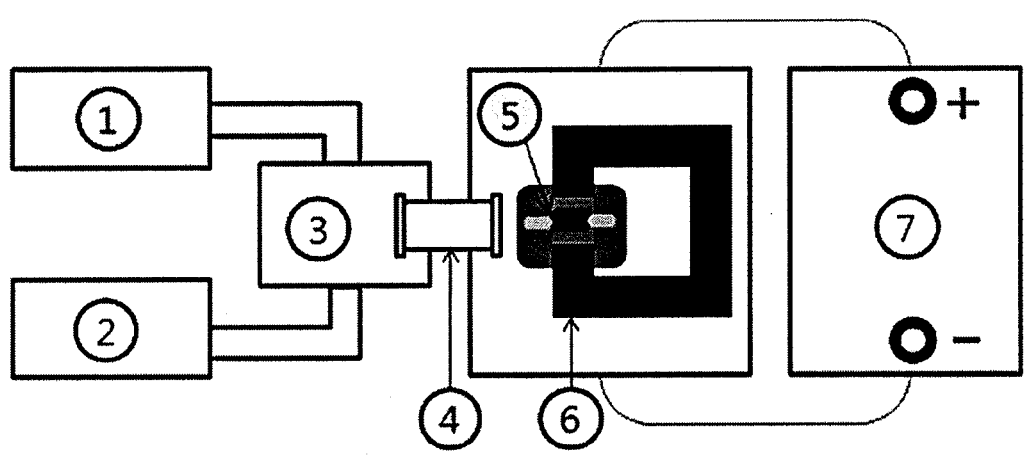
FIG. 2 is a schematic diagram of a magnetic sensor biochip for biometry which is composed of a nanovoltmeter (①), a current source (②), a current-voltage controller (③), a junction for microelectrodes (④), a magnetic sensor (⑤), an electromagnet (⑥), and a power source for operating the electromagnet (⑦)

A magnetic sensor biochip for biodosimetry was fabricated. To begin with, a thiol-caped single-stranded DNA (HS-ssDNA) was synthesized (by Genotech), and was then absorbed and immobilized to the surface of a gold electrode-coated magnetic sensor. Mercaptohexanol (MCH) was applied to the surface to form an MCH layer so that HS-ssDNA was bound to the surface only via the terminal thiol group while preventing the backbone of the immobilized DNA from being in contact with the magnetic sensor. The biochip thus fabricated is schematically depicted in FIG. 2.

Example 2

Detection of DNA Damage Using Magnetic Sensor Biochip for Biodosimetry

For use in examining whether the magnetic sensor biochip for biodosimetry, fabricated in Example 1, detected DNA damage, a single-stranded DNA complementary to the DNA immobilized to the biochip was synthesized, and conjugated with biotin at the 5' terminus (performed by Genotech). The biotin-conjugated DNA was coupled with a magnetic nanoparticle the surface of which was modified with streptavidin. Subsequently, the magnetic particle-coupled DNA was hybridized with the DNA immobilized to the magnetic sensor biochip for biodosimetry to form a DNA duplex before the biochip was exposed to radiation with a dose of 0.05 Gy. Electric signals were monitored with a change in the magnetic field of the magnetic sensor and with time. The results are shown in FIGS. 3 and 4, respectively.

Figure 3:
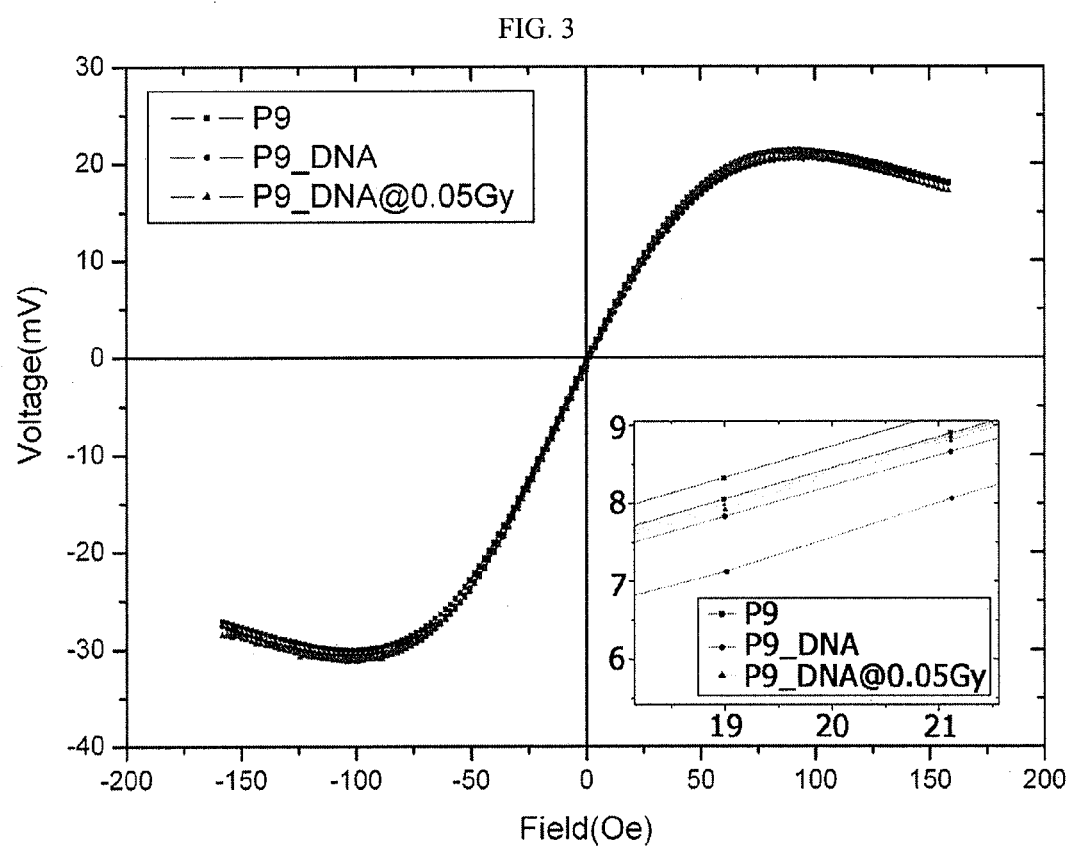
FIG. 3 is a graph showing electric signal profiles of mayuetic sensor biochips.

As is understood from the data of FIG. 3, electric signals were detected at lower levels from the DNA-hybridized biochip (P9_DNA) than the non-hybridized biochip (P9), and were increased upon the exposure of the DNA-hybridized biochip to radiation (P9_DNA@0.05 Gy).

Figure 4:
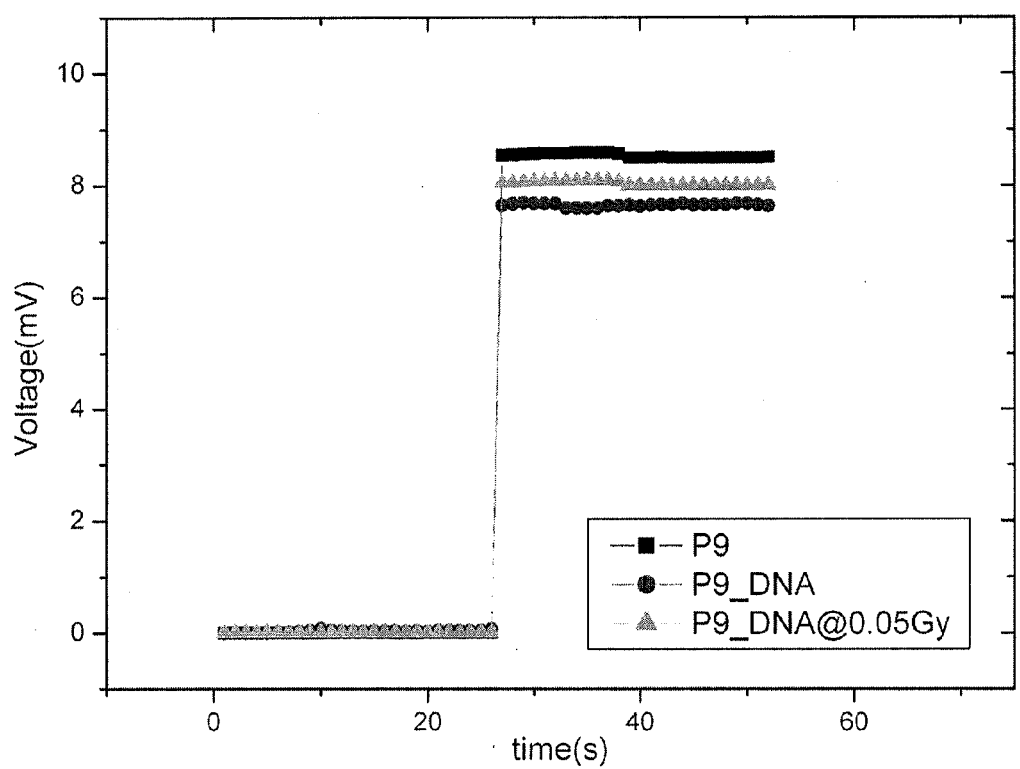
FIG. 4 is a voltagram showing electric signal profiles of magnetic sensor biochips with time.

In the presence of a constant magnetic field, as can be seen in FIG. 4, electric signals were decreased at 25 sec in the DNA-hybridized biochip (P9_DNA), compared to the non-hybridized biochip (P9), and were increased when the DNA-hybridized biochip (P9_DNA) was exposed to radiation (P9_DNA@0.05 Gy).

Taken together, the data obtained above demonstrate that radiation causes damage to a DNA duplex which, in turn, breaks the bond of the magnetic nanoparticle-coupled DNA, resulting in the secession of the DNA from the influence of the magnetic sensor. That is to say, the magnetic sensor cannot sense the magnetic nanoparticle, generating a difference in electric signal intensity between the damaged DNA and the intact double-stranded DNA. Accordingly, the biochip fabricated in Example 1 could measure a change in biomaterial depending on the absorbed dose of radiation.

Example 3

Resistance of Linker Against Radiation

Figure 5:
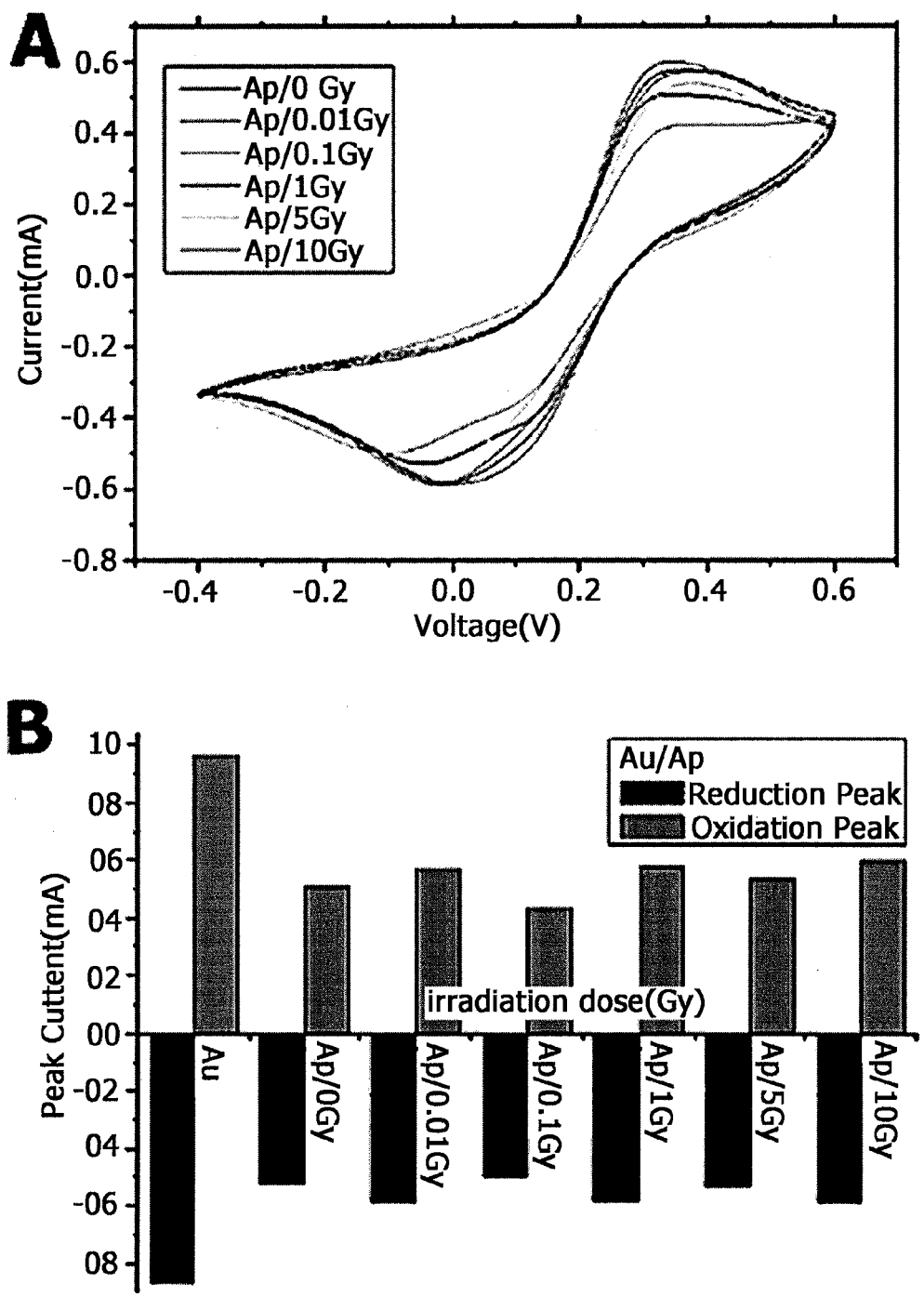
FIG. 5 shows the resistance of a connector between a magnetic sensor biochip and an antibody against radiation in a current-voltage curve (A) and a bar graph of peak current changes (B).

Sys Protein-G (Micobio) or ProLink (Proteogen) was employed to conjugate a linker to the magnetic sensor therethrough. The linker was measured for radiation resistance using cyclic voltammetry (CV). The results are given in FIG. 5.

In FIG. 5B, the first bar represents a measurement from a gold-plated electrode as a control, without conjugation with the linker, while the others starting from the second bar show peak currents measured in the linker-conjugated gold films on electrodes using CV at various doses of radiation (0.01 Gy 10 Gy). As can be seen, the linker (Sys Protein-G) conjugated to the gold film did not experience a change even at a dose of 10 Gy. The results indicate that the amphipathic molecule Sys Protein-G or ProLink is resistant to radiation so that it can be used to conjugate a linker to the surface of the magnetic sensor therethrough.

Although embodiment(s) of the present invention have (has) been disclosed for illustrative purposes, those skilled in the art will appreciate that various modifications, additions and substitutions are possible, without departing from the scope and spirit of the invention as disclosed in the accompanying claims.

Designed to utilize a magnetic sensor in detecting damage to biomaterials in vitro, as described hitherto, the detection method of radiation-induced damage to biomaterials, and the magnetic sensor biochip for biodosimetry in accordance with the present invention, are irrespective of the self-recovery of the organism and thus can accurately determine the degree of the damage. Thanks to their high sensitivity, in addition, the method and the biochip according to the present invention are predicted to detect biomaterial damage by exposure to even a low dose of radiation. Moreover, the magnetic sensor can be conjugated with various linkers which expand a broad spectrum of targets to be measured for radiation-induced damage. In addition, the present invention may be expected to have applications in the measurement of biomaterial damage caused by chemicals or other factors as well as radiation.

What is claimed is:

1. A method for detecting radiation-induced damage of a biomaterial, comprising:
    a) obtaining a biosample exposed to radiation;
    b) conjugating a magnetic nanoparticle with a target biomaterial contained in the biosample;
    c) coupling the magnetic nanoparticle-conjugated target biomaterial with a linker conjugated to a surface of a magnetic sensor to form a complex;
    d) exposing the coupled complex to radiation;
    e) measuring radiation-induced damage to the coupling between the linker and the target biomaterial in an electric signature of the magnetic sensor; and
    f) comparing the measurement with an electric signal of the magnetic sensor detected in a reference sample unexposed to radiation.

2. The method of claim 1, wherein the linker is bound to the target biomaterial.

3. The method of claim 1, wherein the linker is selected from the group consisting of DNA (deoxyribonucleic acid), RNA (ribonucleic acid), a ligand, an antibody, a protein, an enzyme, and a polypeptide.

4. The method of claim 1, wherein the target biomaterial is selected from the group consisting of DNA (deoxyribonucleic acid), RNA (ribonucleic acid), a ligand, an antibody, an antigen, a protein, an enzyme, and a polypeptide.

5. The method of claim 1, wherein the linker is conjugated to the magnetic sensor via an amphipathic molecule that is highly resistant to radiation.

6. The method of claim 1, wherein radiation is selected from the group consisting of a gamma ray, a neutron ray, an X-ray, an electron ray, and an electromagnetic ray with energy of 1 GHz or higher.

7. The method of claim 1, wherein the electric signature of the magnetic sensor is indicative of an absorbed dose of radiation, based on the intensity of a stray field generated when the radiation causes the magnetic nanoparticle to secede from the magnetic sensor.

* * * * *